US012767923B2

(12) United States Patent
Hoffmann et al.

(10) Patent No.: US 12,767,923 B2
(45) Date of Patent: Oct. 20, 2026

(54) METHOD FOR CULTIVATING A MICROORGANISM OF INTEREST AND ASSOCIATED FACILITY

(71) Applicant: KYANOS BIOTECHNOLOGIES, Toulouse (FR)

(72) Inventors: Pierre-Alain Hoffmann, Toulouse (FR); Evelyne Gleyses, Escalquens (FR)

(73) Assignee: KYANOS BIOTECHNOLOGIES, Toulouse (FR)

( * ) Notice: Subject to any disclaimer, the term of this patent is extended or adjusted under 35 U.S.C. 154(b) by 600 days.

(21) Appl. No.: 17/276,142

(22) PCT Filed: Sep. 12, 2019

(86) PCT No.: PCT/EP2019/074424

§ 371 (c)(1), (2) Date: Mar. 13, 2021

(87) PCT Pub. No.: WO2020/053362

PCT Pub. Date: Mar. 19, 2020

(65) Prior Publication Data

US 2022/0049211 A1 Feb. 17, 2022

(30) Foreign Application Priority Data

Sep. 14, 2018 (FR) ..................................... 18 58285

(51) Int. Cl.

*C12N 1/20* (2026.01)
*C12M 1/00* (2006.01)
*C12M 1/26* (2006.01)

(52) U.S. Cl.

CPC ............... *C12N 1/20* (2013.01); *C12M 33/00* (2013.01); *C12M 47/06* (2013.01)

(58) Field of Classification Search

CPC ............ C12N 1/20; C12N 1/12; C12M 33/00; C12M 47/06

See application file for complete search history.

(56) References Cited

U.S. PATENT DOCUMENTS

2013/0157277 A1* 6/2013 Hacker .............. C12N 15/1003 435/6.15
2013/0164834 A1* 6/2013 Licamele ................. C12M 1/04 435/308.1

FOREIGN PATENT DOCUMENTS

WO WO-2014074769 A2 * 5/2014 ............ A01G 33/00

OTHER PUBLICATIONS

R.A Andersen, Algal Culturing Techniques. first ed. p. 431-433. Elsevier Inc., San Diego, 2005. (Year: 2005).*

Meireles Dos Santos A et al. Heterotrophic Cultivation of Cyanobacteria: Study of Effect of Exogenous Sources of Organic Carbon, Absolute Amount of Nutrients, and Stirring Speed on Biomass and Lipid Productivity. Front Bioeng Biotechnol. Feb. 20, 2017;5:12. doi: 10.3389/fbioe.2017.00012. (Year: 2017).*

Islam MS, Shahid A, Kuryllo K, Li Y, Deen MJ, Selvaganapathy PR. Electrophoretic Concentration and Electrical Lysis of Bacteria in a Microfluidic Device Using a Nanoporous Membrane. Micromachines (Basel). Feb. 3, 2017;8(2):45. doi: 10.3390/mi8020045. PMCID: PMC6189965. (Year: 2017).*

Shelford, E. J. and Suttle, C. A.: Virus-mediated transfer of nitrogen from heterotrophic bacteria to phytoplankton, Biogeosciences, 15, 809-819, https://doi.org/10.5194/bg-15-809-2018, 2018. (Year: 2018).*

Kawasaki N, Komatsu K, Kohzu A, Tomioka N, Shinohara R, Satou T, Watanabe FN, Tada Y, Hamasaki K, Kushairi MR, Imai A. Bacterial contribution to dissolved organic matter in eutrophic Lake Kasumigaura, Japan. Appl Environ Microbiol. Dec. 2013;79(23): 7160-8. doi: 10.1128/AEM.01504-13. Epub Sep. 13, 2013. (Year: 2013).*

O'Flaherty, L. M. A. (Jul. 25, 1968). Growth of Aphanizomenon flos-aquae in defined media. ScholarsArchive@OSU. https://ir.library.oregonstate.edu/concern/graduate_thesis_or_dissertations/tm70mz50w (Year: 1968).*

Abed RMM, Kohls K, Leloup J, de Beer D. Abundance and diversity of aerobic heterotrophic microorganisms and their interaction with cyanobacteria in the oxic layer of an intertidal hypersaline cyanobacterial mat. FEMS Microbiol Ecol. Feb. 1, 2018;94(2). doi: 10.1093/femsec/fix183. PMID: 29267956. (Year: 2018).*

Sigitas Sulcius et al., "Establishment of axenic cultures from cyanobacterium *Aphanizomenon flos*—aquae akinetes by micromanipulation and chemical treatment," Algal Research—Biomass Biofuels and Bioproducts, Apr. 2017, pp. 43-50, vol. 23.

Guadalupe Vazquez-Martinez et al., "Strategy to obtain axenic cultures from field-collected samples of the cyanobacterium *Phormidium* animals," J. Microbiological Methods, Apr. 2004, pp. 115-121, vol. 57, No. 1.

Luca Polimene et al., "A substantial fraction of phytoplankton-derived DON is resistant to degradation by metabolically versatile, widely distributed marine bacterium," PLOS ONE, Feb. 3, 2017, pp. 1-13, vol. 12, No. 2.

Gonzalez-Gonalez et al., "Integrated biodiesel and biogas production from microalgae: Towards a sustainable closed loop through nutrient recycling," Renewal and Sustainable Energy Reviews, 2018, vol. 82, pp. 1137-1148, Elsevier.

P. Bohutskyi and E. Bouwer, "Biogas production from algae and cyanobacteria through anaerobic digestion: a review, analysis, and research needs," Adv Biofuels Bioprod, 2013, 873-975.

Young, Bacteriophage Lysis: Mechanism and Regulation, Microbiological Reviews, Sep. 1992, vol. 56, No. 3, pp. 430-481.

(Continued)

*Primary Examiner* — Kade Ariani

(74) *Attorney, Agent, or Firm* — H&I PARTNERS; Chai Im; C. Andrew Im

(57) ABSTRACT

A method for cultivating at least one microorganism of interest, by heterotrophism or mixotrophism, in an aqueous culture medium, contaminating microorganisms developing naturally in the culture medium. A portion of the culture medium with the microorganism of interest and the contaminating microorganisms is sampled. The microorganism of interest and the contaminating microorganisms in the portion of culture medium is physically separated. The contaminating microorganisms thus separated is lysed to produce a lysate. The lysate is reintroduced into the culture medium.

11 Claims, 3 Drawing Sheets

(56) References Cited

OTHER PUBLICATIONS

L. El Hosry et al., "Maillard Reaction: Mechanism, Influencing Parameters, Advantages, Disadvantages, and Food Industrial Applications: A Review," Foods, 2025, vol. 14, No. 11, pp. 1881 (doi.org/10.3390/foods14111881).

Y. Hachisuka et al., "Studies On Spore Germination," J Bacteriol, 1955, vol. 69, No. 4, pp. 407-412 (doi.org/10.1128/jb.69.4.399-406.1955).

Michael T. Guarnieri et al., "Conversion and assimilation of furfural and 5-(hydroxymethyl)furfural by Pseudomonas putida KT2440," Metabolic Engineering Communications, 2017, vol. 4, pp. 22-28 (doi.org/10.1016/j.meteno.2017.02.001).

* cited by examiner

METHOD FOR CULTIVATING A MICROORGANISM OF INTEREST AND ASSOCIATED FACILITY

RELATED APPLICATIONS

This application is a 371 application of PCT/EP2019/074424 filed Sep. 12, 2019, which claims priority from French Patent Application No. 18 58285 filed Sep. 14, 2018, each of which is incorporated herein by reference in its entirety.

FIELD OF THE INVENTION

The present invention is applicable to the field of microbial biomass cultivation by autotrophy and heterotrophy.

More particularly, the present invention relates to a method for cultivating at least one microorganism of interest, by heterotrophy or mixotrophy, and a cultivation facility particularly adapted for the implementation of said cultivation method.

BACKGROUND OF THE INVENTION

Heterotrophy is the need for a living organism to be nourished with pre-existing organic constituents. The term heterotrophy is opposed to that of autotrophy which is the nutrition mode of living organisms which can be nourished solely from inorganic foods in the presence of an external energy source, for example light (photoautotrophy).

Mixotrophy for its part is the nutrition mode of living organisms characterized in that they are capable of being nourished either by autotrophy or by heterotrophy or by both trophic modes simultaneously or primitive bacterial photosynthesis.

When it is sought to produce or use a pure strain, open-medium heterotrophic or mixotrophic methods are not currently applied. Indeed, open medium generally involves the occurrence of contaminations of cultures by various contaminating microorganisms which affect the material yield of the cultivation method due to the consumption by the contaminating microorganism(s), of the nutrients intended for the microorganisms of interest. These contaminating microorganisms also affect the expected quality of the end product (biomass of microorganisms of interest) simply due to the significant presence thereof.

This contamination risk is currently controlled thanks to method confinement and equipment sterilization. However, the investment and operating costs of these cultivation methods in order for them to be carried out under aseptic conditions are substantial and have a direct impact on the production cost of the microorganisms of interest in question or of the metabolites thereof.

Therefore, it would appear to be advantageous to find a solution for producing microorganisms of interest with an acceptable yield on an industrial level, in an open or closed culture medium, without having to be concerned with the sterilization conditions of said culture medium and equipment.

OBJECT AND SUMMARY OF THE INVENTION

To this end, according to a first aspect, the present invention relates to a method for cultivating at least one microorganism of interest, by heterotrophy or mixotrophy, in an aqueous culture medium, contaminating microorganisms developing naturally in said culture medium, characterized in that it comprises:

- a step of sampling a portion of the culture medium comprising the microorganism of interest and contaminating microorganisms;
- a step of physically separating the microorganism of interest and the contaminating microorganisms in said portion of culture medium;
- a step of lysis of the contaminating microorganisms thus separated so as to produce a lysate;
- a step of reintroducing said lysate into the culture medium.

The term culture medium denotes a medium including nutrients enabling the development of the microorganism of interest and the contaminating microorganisms.

The term "portion" denotes a volume sampled per unit of time, for example per day or per hour. Thus, the term "portion" can be considered as a daily or hourly rate, i.e., a volume sampled respectively per day or per hour, in the culture medium. This volume is preferably, per day, greater than or equal to once the volume of the culture medium and, preferably, greater than or equal to three times the volume of the culture medium. More preferably, the sampled portion corresponds to a volume sampled per hour greater than or equal to 1/24th of the total volume of the culture medium.

This volume sampled daily makes it possible to maintain a quantity of microorganism of interest and of contaminating microorganisms compatible with correct operation of the method according to the present invention.

This cultivation method has the advantage of enabling the open- or closed-medium cultivation of microorganisms of interest without affecting the yield of microorganism of interest because, the contaminants normally being disruptive for open-medium cultivation, are useful for the development of the microorganism(s) of interest according to the method according to the present invention. Indeed, the lysate of contaminating microorganisms represents a digestible source of nutrition for the microorganism of interest, particularly of organic carbon. Open-medium cultivation being enabled by this cultivation method, the investment and operating costs of said method are advantageously minimized in that aseptic conditions are not necessary.

According to preferred implementations, the invention further complies with the following features, embodied separately or in each of the technically feasible combinations thereof.

In a particular implementation, the physical separation step includes a step of gravitational filtration or separation so as to separately obtain the microorganism of interest on one hand and the contaminating microorganisms on the other.

According to a particular implementation, the microorganism of interest separated by the separating step is reintroduced into the culture medium, alone or in a mixture with the lysate.

According to a particular implementation, the aqueous culture medium is initially devoid of organic carbon.

In a particular implementation wherein the cultivation method is by mixotrophy, and wherein the aqueous culture medium is initially devoid of organic carbon, the microorganism of interest is left in autotrophic culture for a time t before the sampling step.

Preferably, the time t is selected so as to obtain a concentration of microorganism of interest in the culture medium between $5\cdot10^5$ cells per milliliter and $1\cdot10^7$ cells per milliliter. Furthermore, cultivation by autotrophy for the time t makes it possible advantageously to validate the correct physiological state of the microorganism of interest and establish reference data in respect of the growth performances thereof.

A switch from autotrophic mode to mixotrophic mode is carried out by mixing the lysate of contaminating microorganisms with the microorganism of interest, said lysate particularly supplying a nutrient source of organic carbon to the microorganism of interest. The heterotrophic mode is all the more reinforced by a step of supplying organic carbon, supplied by a source other than the lysate of contaminating microorganisms, in the culture medium.

To this end, according to a particular implementation, the method includes a step of supplying organic carbon to the culture medium. This supply of organic carbon can be carried out directly in the culture medium, in the lysate, to the microorganism of interest separated by physical separation, in the separated lysate/microorganism of interest mixture, or in a combination of at least two thereof.

In a particular implementation, the culture method comprises a step of concentrating the contaminating microorganisms separated by the physical separation step. The step of concentrating the contaminating microorganisms is advantageous in that it enables a lysis of a greater number of contaminating microorganisms during the lysis step.

According to a particular implementation example, the concentration step includes a step of gravitational filtration or separation so as to separately obtain the concentrated contaminating microorganisms on one hand and culture medium devoid of contaminating microorganisms on the other. This has the advantage of enabling the recycling of the culture medium devoid of contaminating microorganisms. Furthermore, this particularly has the advantage of reducing the costs of lysis due to a reduction in the volume of contaminating microorganisms to be lysed following the concentration.

In a particular implementation, the culture medium includes several different microorganisms of interest, said method including upstream from the physical separation step, a prior step of isolating a single type of microorganisms of interest selected or a set of different microorganisms of interest selected within said sampled portion, such that when this portion undergoes the physical separation, it only comprises said single type of microorganisms of interest selected or said set of different microorganisms of interest selected.

According to a particular implementation, the cultivation method comprises a repeated cycle of the steps thereof. In an implementation example, the method includes a repeated cycle of at least the steps of sampling, physical separation, lysis, and reintroduction. Preferably, said repeated cycle also includes the concentration step, and/or the step of supplying organic carbon.

Due to this mixture of trophic modes within a cyclic cultivation method, the method according to the present invention can be described as a method for cultivating at least one microorganism of interest by cyclotrophy.

According to a preferred implementation example, said at least one microorganism of interest is the cyanobacterium *Aphanizomenon flos-aquae* (AFA).

According to a second aspect, the present invention relates to a facility for cultivating at least one microorganism of interest, by heterotrophy or mixotrophy, including:

- at least one open or closed culture compartment designed to receive an aqueous culture medium, said at least one microorganism of interest and contaminating microorganisms;
- at least one separating apparatus designed to perform at least one physical separation of the microorganism of interest and the contaminating microorganisms within a portion of the culture medium;
- a lysis device designed to perform a lysis of the contaminating microorganisms separated by the physical separation so as to produce a lysate;
- transport means designed for at least:
  - sampling a portion of the culture medium comprising the microorganism of interest and contaminating microorganisms;
  - reintroducing said lysate into the culture compartment.

The particular advantages, aims and features of the facility according to the present invention being similar to those of the method according to the present invention, they are not repeated here.

According to preferred embodiments, the invention further complies with the following features, implemented separately or in each of the technically feasible combinations thereof.

In a particular embodiment, the transport means are furthermore designed to unify the lysate with the microorganism of interest isolated by physical separation, so as to form a mixture, and reintroduce said mixture into the culture compartment.

In a particular embodiment, the transport means are furthermore designed to supply organic carbon to the culture medium directly in the culture compartment, in the lysate, in the separated lysate/microorganism of interest mixture or to the microorganism of interest separated by physical separation. This supply of organic carbon originates from a source other than the lysate of contaminating microorganisms.

In a particular embodiment, the cultivation facility includes at least one concentration system designed to concentrate the contaminating microorganisms isolated by physical separation.

In a particular embodiment, the transport means include means:

- for generating a first flow of culture medium comprising the microorganism of interest and contaminating microorganisms, from the culture compartment to the separating apparatus;
- for generating a second flow of the microorganism of interest outflowing from the separating apparatus;
- for generating a third flow of contaminating microorganisms from the separating apparatus to the concentration system;
- for generating a fourth flow of concentrated contaminating microorganisms from the concentration system to the lysis device;
- for generating a fifth flow of culture medium devoid of contaminating microorganisms from the concentration system to the culture compartment;
- for generating a sixth flow of lysate from the lysis device to the culture compartment;
- for generating a seventh flow of organic carbon outflowing from an organic carbon tank;
- for unifying the second flow, the sixth flow and the seventh flow so as to form an eighth single current flow to the culture compartment.

In a particular embodiment, the cultivation facility includes a device for draining contaminating microorganisms. Preferably, it consists of a device for draining concentrated contaminating microorganisms.

In a particular embodiment, the cultivation facility includes a device for draining culture medium devoid of contaminating microorganisms and microorganism of interest.

In a particular embodiment, the cultivation facility includes a device for collecting the microorganism of interest.

BRIEF DESCRIPTION OF THE FIGURES

The invention will be better understood on reading the following description, given by way of non-limiting example, and with reference to the figures which represent.

DETAILED DESCRIPTION OF THE INVENTION

It is noted as of now that the figures are not to scale.

More generally, the scope of the present invention is not limited to the implementations and embodiments described above by way of non-limiting examples, but extends on the contrary to any modifications to the scope by a person skilled in the art. Each feature of an embodiment can be advantageously implemented separately or combined with any other feature of any other embodiment.

Figure 1:
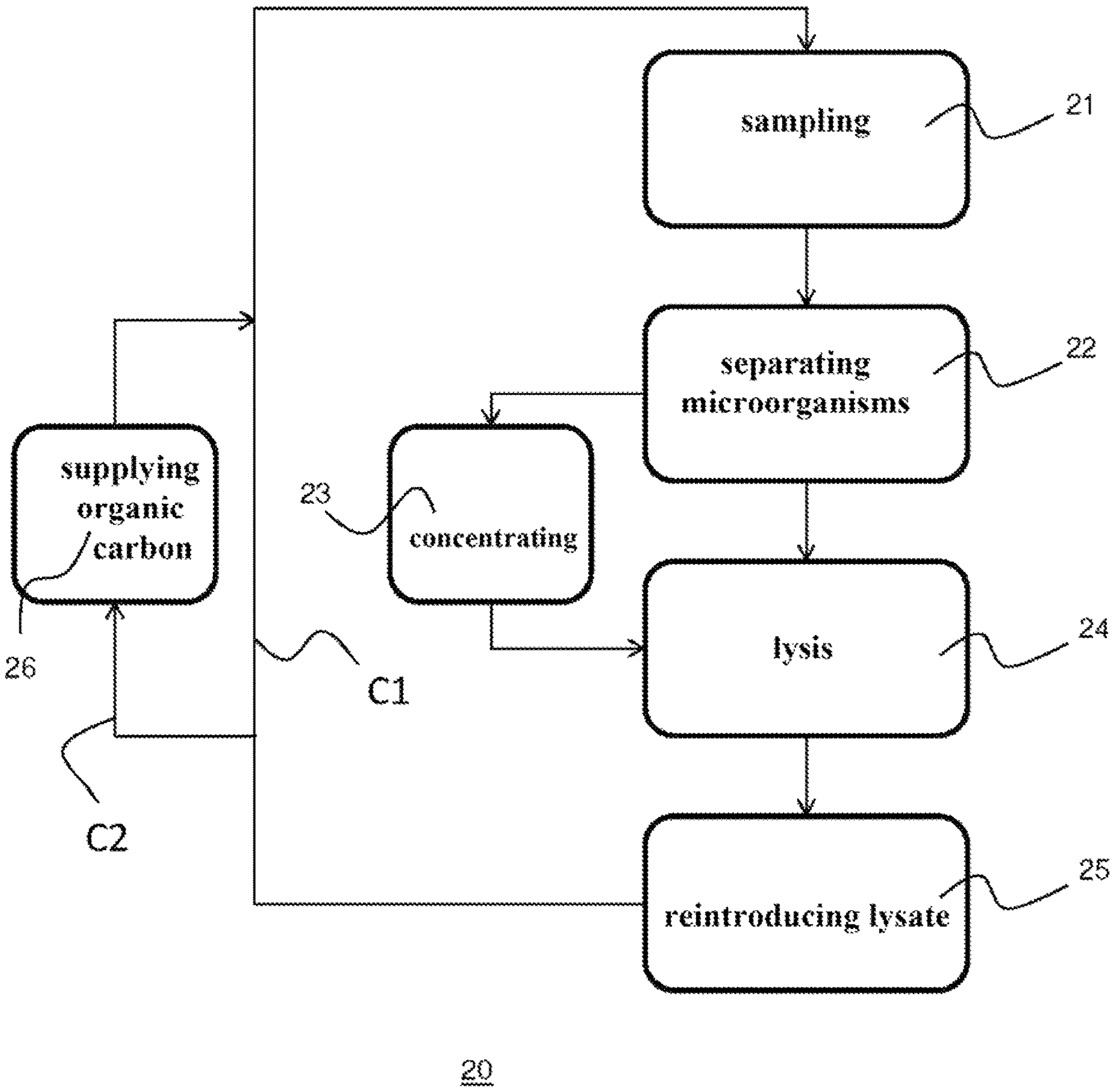
FIG. 1: illustrates the steps comprised by the cultivation method according to the present invention according to implementations.

FIG. 1 illustrates a method 20 for cultivating at least one microorganism of interest, by heterotrophy or mixotrophy, in an aqueous culture medium, contaminating microorganisms developing naturally in said culture medium, according to a particular implementation. The method includes a step 21 of sampling a portion of the culture medium comprising the microorganism of interest and contaminating microorganisms. Preferably, the method 20 is carried out by mixotrophy, the aqueous culture medium being initially devoid of organic carbon and the microorganism of interest is left in autotrophic culture for a time t before the step 21.

The method 20 includes a step 22 of physically separating the microorganism of interest and the contaminating microorganisms in the portion of the culture medium.

The embodiment of the physical separation step 22 can be based on a morphological or phenotypic difference between the microorganisms of interest and the contaminating microorganisms. For example, it can consist of a difference in size, shape, surface properties, density, aggregation or flocculation tendency.

According to an implementation example, the physical separation step 22 includes a step of gravitational filtration or separation so as to separately obtain the concentrated contaminating microorganisms on one hand and the nutrient medium on the other. An example of filtration used in a preferred implementation is tangential filtration or frontal filtration. The filtration can be performed using a membrane.

The method 20 further includes an optional step 23 of concentrating the contaminating microorganisms isolated in step 22.

The optional step 23 of concentrating the contaminating microorganisms can be based on a morphological or phenotypic feature of the contaminating microorganisms. For example, it can consist of their size, their shape, their surface properties, their density, their tendency to aggregate or flocculate.

According to a preferred implementation, the concentration step 23 includes a step of gravitational filtration or separation so as to separately obtain the concentrated contaminating microorganisms on one hand and culture medium devoid of contaminating microorganisms on the other. As for the physical separation, in a particular implementation, an example of filtration used is tangential filtration or frontal filtration, and the filtration can particularly be performed using a membrane.

The method 20 includes a step 24 of lysis of the contaminating microorganisms separated by the physical separation so as to produce a lysate. This lysate advantageously represents nutrients digestible by the microorganism of interest, particularly organic carbon. In a particular implementation, the lysis step 24 can comprise a chemical lysis and/or a thermal lysis and/or a mechanical lysis, of the contaminating microorganisms.

The method 20 also includes a step 25 reintroducing said lysate into the culture medium.

According to a preferred embodiment example, the step 25 is carried out such that the lysate is reintroduced into the culture medium in a mixture with the microorganism of interest isolated by the physical separation step 22.

Finally, the method 20 includes an optional step 26 of supplying organic carbon to the culture medium. This organic carbon originates from a source other than the lysate of contaminating microorganisms. Indeed, this supply of organic carbon in step 26 is an additional supply to the supply of nutrients (of which organic carbon) present in the lysate of contaminating microorganisms.

Preferably, the step 26 of supplying organic carbon in the culture medium is performed by introducing said organic carbon into the lysate and microorganism of interest mixture, into the lysate alone, into the microorganism of interest isolated by the physical separation step 22 or into the aqueous culture medium directly.

According to a preferred implementation, the method includes a repeated cycle of steps 21 to 26, steps 23 and 26 remaining optional.

According to an implementation example wherein the cultivation method is by heterotrophy, the step 26 of supplying organic carbon is introduced in a cycle C1 of steps 21 to 25, after the implementation of at least one cycle C1, thus creating a cycle C2 of steps 21 to 26 which is hereinafter repeated as many times as is necessary.

According to an implementation example wherein the cultivation method 20 is by mixotrophy, with the aqueous culture medium initially devoid of organic carbon and the microorganism of interest left in autotrophic culture for a time t before step 21, step 26 of supplying organic carbon is introduced from the implementation of the first cycle of steps 21 to 25, before the sampling step 21, thus commencing the method 20 with the cycle C2, said step 26 being carried out by supplying organic carbon directly into the aqueous culture medium at least in the first cycle C2.

In a particular implementation, the cultivation method 20 comprises a step (not shown in the figures) of clarifying the lysate obtained by means of the lysis step 24, a concentration and/or an adjustment of pH of the lysate, before the reintroduction step 25.

Figure 2:
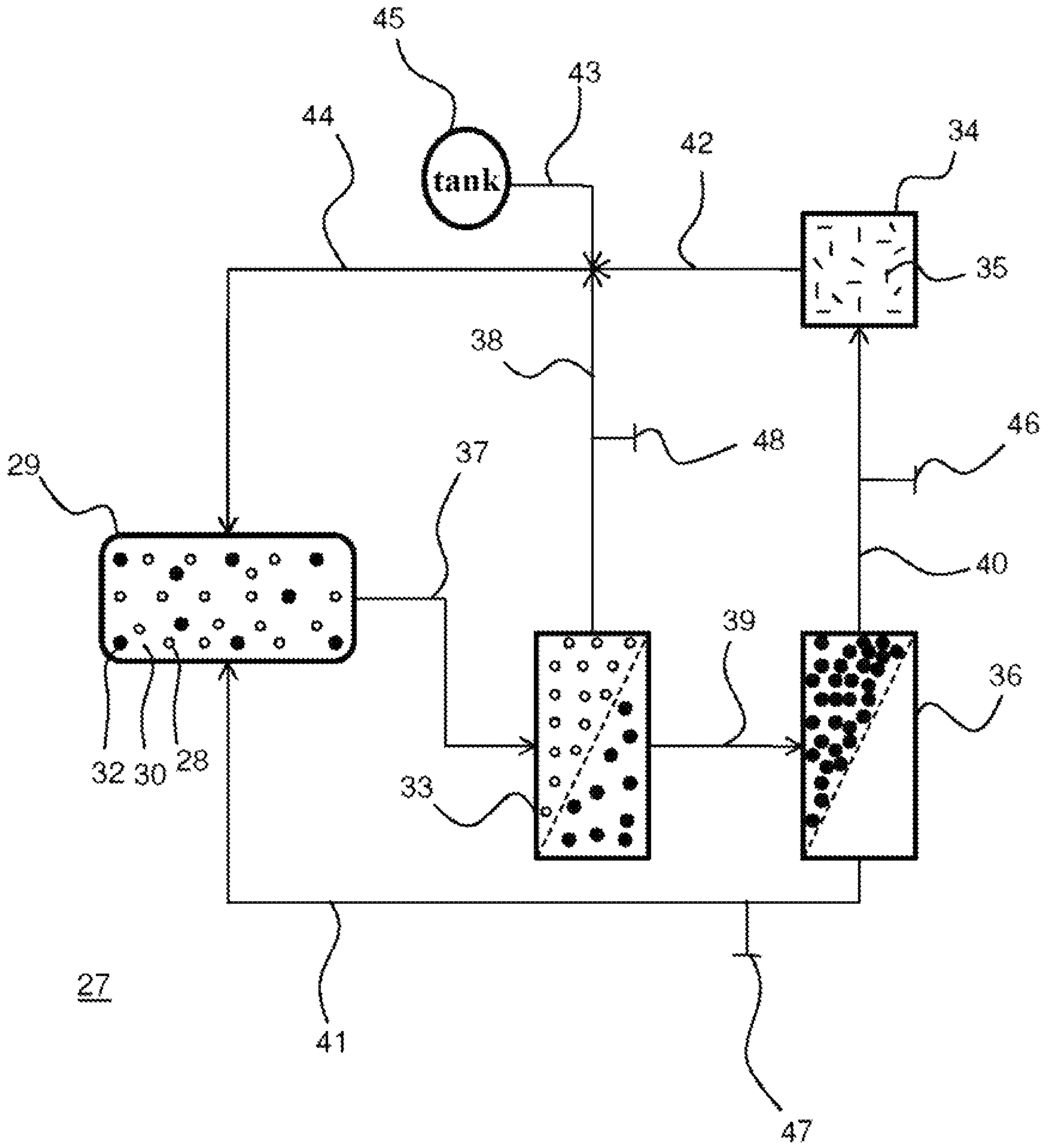
FIG. 2: illustrates a cultivation facility according to the present invention according to an embodiment.

FIG. 2 illustrates a facility 27 for cultivating at least one microorganism of interest 28 by heterotrophy or mixotrophy.

The facility does not advantageously need to be under aseptic conditions, either beforehand, or during the use therefore for cultivation.

The facility 27 includes an open or closed culture compartment 29 designed to receive an aqueous culture medium 30, said at least one microorganism of interest 28 and contaminating microorganisms 32.

The facility 27 further includes at least one separating apparatus 33 designed to perform at least one physical separation of the microorganism of interest 28 and the contaminating microorganisms 32 within a portion of the culture medium 30.

The facility 27 includes a lysis device 34 designed to perform a lysis of the contaminating microorganisms 32 separated so as to produce a lysate 35.

According to a particular embodiment, the facility further includes at least one concentration system 36 designed to concentrate the contaminating microorganisms 32 separated before the lysis thereof.

The facility 27 includes transport means designed for at least:

- sampling a portion of the culture medium 30 comprising the microorganism of interest 28 and contaminating microorganisms 32;
- reintroducing the lysate 35 into the culture compartment 29.

Preferably, the transport means are furthermore designed to unify the lysate 35 with the separated microorganism of interest 28, so as to form a mixture and reintroduce said mixture into the culture compartment 29.

Preferably, the transport means are designed to supply organic carbon to the culture medium 30 directly in the culture compartment 29 or to the lysate 35 or to the microorganism of interest 28 separated by the physical separation or to the mixture of lysate 35 and microorganism of interest 28 or in a combination of at least two thereof.

According to a preferred embodiment, the transport means include means:

- for generating a first flow 37 of culture medium 30 comprising the microorganism of interest 28 and contaminating microorganisms 32, from the culture compartment 29 to the separating apparatus 33;
- for generating a second flow 38 of the microorganism of interest 28 outflowing from the separating apparatus 33;
- for generating a third flow 39 of contaminating microorganisms 32 from the separating apparatus 33 to the concentration system 36;
- for generating a fourth flow 40 of concentrated contaminating microorganisms 32 from the concentration system 36 to the lysis device 34;
- for generating a fifth flow 41 of culture medium 30 devoid of contaminating microorganisms, from the concentration system 36 to the culture compartment 29;
- for generating a sixth flow 42 of lysate 35 from the lysis device 34 to the culture compartment 29;
- for generating a seventh flow 43 of organic carbon;
- for unifying the second flow 38, the sixth flow 42 and the seventh flow 43 so as to form an eighth single current flow 44 to the culture compartment 29.

According to a particular embodiment example, the facility 27 comprises an organic carbon tank 45. The seventh flow 43 is preferably generated such that it comes out of the tank 45.

The fifth flow 41 is preferably devoid of microorganisms of interest.

According to a particular embodiment, the means for generating the different flows include at least a motor and/or a pump (not illustrated in the figures).

In a particular embodiment, the facility 27 includes a first device 46 for draining contaminating microorganisms 32, a second device 47 for draining culture medium 30 devoid of microorganisms of interest and contaminating microorganisms and a device 48 for collecting the microorganism of interest 28.

The method 20 for cultivating at least one microorganism of interest 28, by heterotrophy or mixotrophy, is detailed hereinafter according to an implementation wherein a facility 27 according to the present invention is particularly used according to one of the embodiments thereof:

An aqueous culture medium 30 and microorganism of interest 28 is previously introduced into the culture compartment 29. The microorganism of interest 28 is preferably left in autotrophic culture for a time t.

Organic carbon is then introduced directly into the culture compartment 29 according to step 26, via the seventh flow 43 of organic carbon outflowing from the tank 45. The culture then switches to mixotrophy and contaminating microorganisms 32 develop in the culture medium 30 with the microorganism of interest 28.

In step 21, the sampling of a portion of the culture medium 30 comprising the microorganism of interest 28 and the contaminating microorganisms 32 is carried out by generating the first flow 37 of culture medium 30 from the compartment 29 to the separating apparatus 33.

In the separating apparatus 33, the step 22 of physically separating the microorganism of interest 28 and the contaminating microorganisms 32 in the portion of the culture medium 30 sampled is performed. Preferably, this step 22 is carried out by tangential membrane filtration.

After the physical separation step 22, the second flow 38 of microorganism of interest 28 outflowing from the separating apparatus 33 is generated, as well as the third flow 39 of contaminating microorganisms 32 from the separating apparatus 33 to the concentration system 36.

In the concentration system 36, the optional step 23 of concentrating the contaminating microorganisms 32 separated by the step 22 takes place. Preferably, this step 23 is carried out by tangential membrane filtration. This step 23 can be considered as a second physical separation for separating, on one hand, the contaminating microorganisms 32 in a concentrated manner and, on the other, culture medium 30 devoid of contaminating microorganisms 32 and microorganism of interest 28.

After this step 23, the fourth flow 40 of concentrated contaminating microorganisms 32 is generated from the concentration system 36 to the lysis device 34, and the fifth flow 41 of culture medium 30 devoid of contaminating microorganisms 32 and of microorganism of interest 28, is generated from the concentration system 36 to the culture compartment 29.

In the lysis device 34, the step 24 of lysis of the separated and concentrated contaminating microorganisms 32 then takes place, so as to produce the lysate 35.

The third flow 39 is directly targeted toward the lysis device 34 in an implementation where the concentration step 23 does not take place. In such a particular implementation, the lysis step 24 is carried out on the separated contaminating microorganisms 32 originating directly from the separating apparatus 33 via the third flow 39.

Then, in the reintroduction step 25, the lysate 35 is reintroduced into the culture medium 30 in the culture compartment 29 by generating the sixth flow 42 of lysate 35. Preferably, the second flow 38 of microorganisms of interest 28 and the sixth flow 42 of lysate 35 are unified so as to form a current mixture to the compartment 29.

This cycle C2 of the cultivation method can be repeated several times.

After the first cycle C2, in the steps 26 of each following cycle C2, the seventh flow 43 of organic carbon outflowing from the tank 45 which is generated is preferably unified with the second flow 38 and the sixth flow 42 so as to form the single eighth flow 44 of current mixture to the compartment 29 wherein it is reintroduced.

Example Applied to the Cultivation of *Aphanizomenon flos-aquae* (AFA) by Mixotrophy in Open Medium Microorganisms Used The microorganism of interest 28 used in this study is an isolated *Aphanizomenon flos-aquae* (AFA) strain. AFA is a cyanobacterium of industrial and commercial interest.

Model contaminating microorganisms 32 are formed by a mixture of 5 strains of bacilli having different morphological and phenotypic characteristics. This mixture is presented in the form of a live bacterial solution, concentrated and presented in liquid formulation. The solution marketed under the reference "Bactilit™" by the company CG PACKAGING can for example be used.

In order to simplify the method, the contaminating microorganisms 32 are initially introduced into the cyanobacteria culture at a rate of one cell of the microorganism of interest 28 for one cell of contaminating microorganism 32. Moreover, it should be noted that a filament is considered as a cyanobacteria cell, regardless of its size.

Culture Media

The culture medium used is a BG11 medium (detailed composition provided in tables A to D), native for cultivation by autotrophy, or, supplemented with whey powder at a final concentration of 4.5 $g \cdot L^{-1}$ for cultivation by mixotrophy.

TABLE A composition of stock solution 1

| Product | Concentration g/L |
|---|---|
| $Na_2MgEDTA$ | 0.1 |
| Ferric Ammonium Citrate | 0.6 |
| Citric acid, $H_2O$ | 0.6 |
| $CaCl_2$, $2H_2O$ | 3.6 |
| Osmosed water, sterilization 20 minutes at 121° C. or filtration (storage at 4° C.) | |

TABLE B composition of stock solution 2

| Product | Concentration g/L |
|---|---|
| $MgSO_4$, 7H2O | 7.5 |
| Osmosed water, sterilization 20 minutes at 121° C. or filtration (storage at 4° C.) | |

TABLE C composition of stock solution 3

| Product | Concentration g/L |
|---|---|
| K2HPO4 | 0.6 |
| Osmosed water, sterilization 20 minutes at 121° C. or filtration (storage at 4° C.) | |

TABLE D composition of BG11 nutrient medium solution

| Product | Concentration g/L or mL/L |
|---|---|
| Stock solution 1 (mL) | 10 |
| Stock solution 2 (mL) | 10 |
| Stock solution 3 (mL) | 10 |
| $Na_2CO_3$ (g) | 0.02 |
| $NaNO_3$ (g) | 1.5 |
| Osmosed water, pH adjusted to 9, sterilization 20 minutes at 121° C. | |

Culture Operating Conditions

The AFA culture is produced in an air-conditioned room in which the temperature is regulated at 25±1° C. The borosilicate glass culture compartment 29 (total volume=250 mL, culture volume=200 mL, effective height=70 mm, effective diameter=60 mm) is equipped with blade stirring (water propeller type mobile stirring device, mobile device diameter=30 mm, stirring speed=60 rpm).

Light is supplied by a light-emitting diode panel (irradiance of photosynthetically active radiation measured on the outer wall of the reaction vessel=200 $\mu mol \cdot s^{-1} \cdot m^{-2}$).

The culture inoculation rate was set at $5 \cdot 10^5$ and $1 \cdot 10^6$ $cells \cdot mL^{-1}$.

Unitary Operations and Operating Conditions for Physically Separating the Microorganism of Interest from the Contaminating Microorganisms and for Concentrating the Contaminating Microorganisms As regards the physical separation between *Aphanizomenon flos-aquae* and the model contaminating microorganisms (various strains of bacilli in a mixture), the method used consists of a first tangential membrane filtration.

The concentration of the model contaminating microorganisms makes use of a second physical separation between said contaminating microorganisms and the BG11 culture medium carried out by a second tangential membrane filtration.

The first filtration makes use of a membrane having a porosity of 5 μm. It is possible, for the first tangential filtration, to use a membrane having a porosity between 0.65 μm and 20 μm, and preferably between 1.2 μm and 20 μm, preferably between 3 μm and 20 μm, and more preferably between 5 μm and 20 μm.

The second filtration makes use of a membrane having a porosity of 0.2 μm. It is possible, for the second tangential filtration, to define a porosity threshold less than 5 μm, and preferably less than 3 μm, and preferably less than 1.2 μm, and preferably less than 0.65 μm, and preferably less than 0.2 μm.

Concerning the permeation rate to be applied for the first tangential filtration (i.e., the sampling rate of a portion of the culture medium), a daily rate greater than or equal to one time the volume of the cultivation facility 27, and preferably greater than or equal to three times the volume of the cultivation facility 27, is preferably selected.

Concerning the tangential rates to be applied in the first tangential filtration, it is preferable to apply rates less than or equal to 2.1 $m \cdot s^{-1}$, and preferably less than or equal to 0.7 $m \cdot s^{-1}$.

Unitary Operations and Operating Conditions for the Lysis of the Contaminating Microorganisms Concerning the lysis of the contaminating microorganisms, a hot alkaline lysis is used. A volume of 5N soda was added to the concentrated contaminating microorganism solution in order to reach a final concentration of 0.1N. This solution was then kept at 70° C. for 10 minutes before being cooled.

Results Obtained

Before the sampling step 21 of the cultivation method, the microorganism of interest is left in autotrophic culture in the culture medium 30 for a time t in order to validate the correct physiological state of the strain and establish reference data in respect of the growth performances. After the time t, the method is launched in a repeated cyclical fashion according to the cycle C2 with the step 26 of supplying organic carbon and the concentration step 23.

In autotrophy, a quick observation makes it possible to demonstrate that the strain is growing with a first phase, up to 100 h, corresponding to exponential growth then, a second phase of linear growth, between 100 h and 600 h. Finally, a deceleration phase is observed after 600 h. These trends are conventionally observed in the case of non-balanced growth, i.e., in the case where an environmental factor becomes limiting. This may consist of a nutritional factor (substrate, metabolism product) or physicochemical factors. In this case, it is reasonable to hypothesize that the light energy can become limiting beyond a certain cell density (shading phenomenon).

By applying a linear regression, it is possible to determine a representative equation of the growth rate, namely: $y=0.002x+0.4453$.

It is also possible to evaluate the volume productivity of the strain thanks to the mass concentration measurements of the microorganism of interest.

The cellular concentration in the cultures is estimated by measuring the absorbance of a liquid sample. The absorbance measurement of the medium is carried out at 600 nm by means of a spectrophotometer. This absorbance (or optical density) is considered as having a linear relationship with the concentration (Beer-Lambert law, Abs=ε.I.C) for values between 0.1 and 0.4 units. Dilutions are made so as to be situated in this validity range.

The mass cellular concentration is also measured by measuring the suspended solids (SS). The concentration of suspended solids ([SS]) is estimated by weighing the dry mass of a known volume of cell suspension. The latter is filtered on a membrane of pore size 0.45 μm (Φ=4.7 cm) previously dried at 60° C. and 200 mm Hg for 24 hours and weighing. After filtration, the membrane and the cell deposit are dried under the same conditions and then weighed. The difference in mass with respect to the volume makes it possible to obtain the concentration of suspended solids in the filtered suspension.

The microbial growth is evaluated in terms of doubling time (or generation time, $t_g$) and volume productivity ($r_x$).

The autotrophic growth parameters of the AFA strain are a maximum suspended solid concentration ($[SS]_{max}$) of 0.75 $g \cdot L^{-1}$ and a maximum volume productivity ($r_x$ max) of $26 \cdot 10^{-3}$ $g \cdot L^{-1} \cdot j^{-1}$.

When the method according to the present invention is implemented by mixotrophy, i.e., when the first cycle C2 is initiated starting with the step 26 of supplying organic carbon to the culture medium, a gain in productivity is observed despite the consumption of some of the organic carbon supplied by the contaminating microorganisms. Indeed, adding lysate of contaminating microorganisms to the culture makes it possible to supply highly digestible organic carbon and therefore, to recycle some of the initial organic carbon consumed by the contaminating microorganisms.

Calculation of the Productivity Yield Gain for Cultivating AFA with the Cultivation Method by Mixotrophy The mass concentration of AFA was recorded over time (every hour for 150 h) in a native BG11 culture medium (autotrophy: Control). In parallel, the mass concentration of AFA was recorded over time in BG11 culture media during implementation tests of the cultivation method according to the present invention carried out by mixotrophy, the step of reintroducing the lysate into the culture medium being carried out with different lysate concentrations (0.1 g/L or 1 g/L or 5 g/L) according to the tests.

Figure 3:
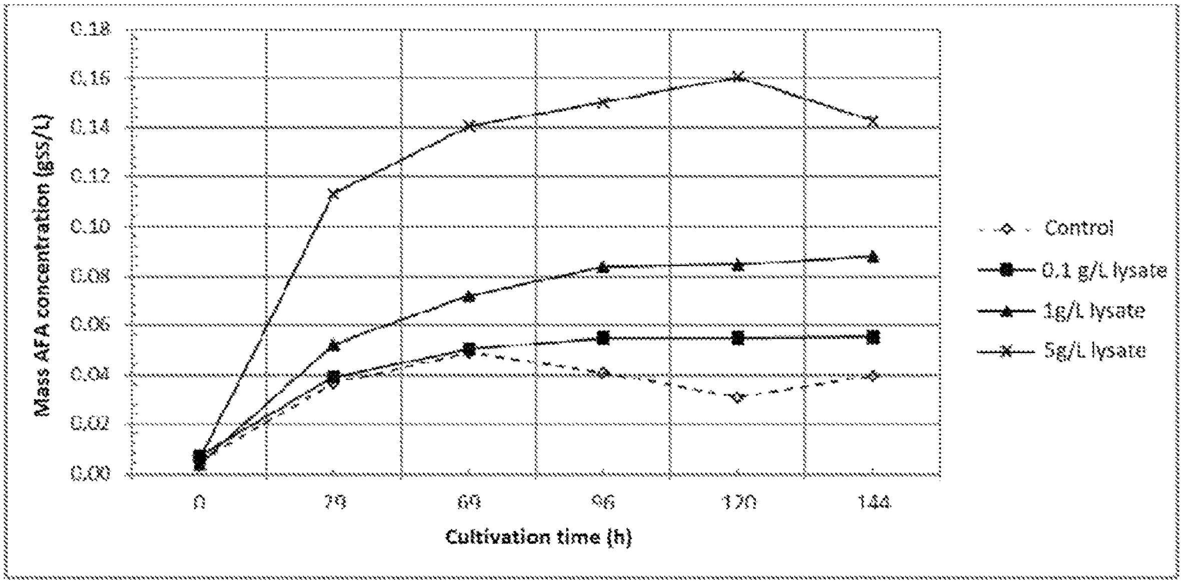
FIG. 3: graph of the progression of the mass concentration of *Aphanizomenon flos-aquae* (AFA) over time in a culture medium according to the implementation of the method according to the present invention by autotrophy or by mixotrophy with reintroduction of different lysate concentrations.

The progression of the mass concentration of AFA over time can be seen in the graph in FIG. 3.

These results indicate that adding lysate makes it possible to increase the productivity and the maximum AFA concentration in the cultures. This effect is all the more pronounced as the lysate concentrations are high for values between 0.1 and 5 g/L.

A stoichiometric analysis shows that adding 5 g/L of lysate (corresponding to 165 mg of organic carbon per liter) makes it possible to increase the maximum AFA titer by 111 mg of AFA per liter. This being equivalent to a heterotrophic production yield of microorganism of interest of 0.6 grams of AFA per gram of organic carbon supplied by the lysate.

A kinetic analysis shows that adding 5 g/L of lysate makes it possible to increase, for up to 29 h of culture, the AFA productivity from 26.4 mg of AFA per liter per hour to 91.2 mg of AFA per liter per hour, i.e., +340%.

The invention claimed is:

1. A method for cultivating at least one microorganism of interest, by heterotrophy or mixotrophy, in an aqueous culture medium, contaminating microorganisms developing naturally in the aqueous culture medium, the method comprising:

(a) sampling a portion of the aqueous culture medium comprising the at least one microorganism of interest and the contaminating microorganisms, the at least one microorganism of interest being a cyanobacterium;

(b) physically separating the at least one microorganism of interest and the contaminating microorganisms in the portion of aqueous culture medium by using filtration;

(c) performing an alkaline chemical lysis and a thermal lysis of the contaminating microorganisms thus separated to produce a lysate comprising an organic carbon;

(d) reintroducing the lysate into the aqueous culture medium comprising the at least one microorganism of interest and the contaminating microorganisms to supply digestible source of nutrition to the at least one microorganism of interest; and (e) reintroducing the at least one microorganism of interest separated at step b) into the aqueous culture medium comprising the at least one microorganism of interest and the contaminating microorganisms, alone or in a mixture with the lysate.

2. The cultivation method of claim 1, further comprising supplying additional organic carbon into the aqueous culture medium.

3. The cultivation method of claim 2, by mixotrophy, wherein the aqueous culture medium is initially devoid of the organic carbon and the at least one microorganism of interest is left in autotrophic culture for a predetermined time before supplying the organic carbon and before sampling the portion of the aqueous culture medium.

4. The cultivation method of claim 1, further comprising concentrating the contaminating microorganisms separated in the portion of aqueous culture medium.

5. The cultivation method of claim 1, wherein the aqueous culture medium comprises different microorganisms of interest, the method comprises upstream from the physically separating step, a prior step of isolating a single type of microorganisms of interest or a set of different microorganisms of interest selected within the sampled portion, such that when the sample portion undergoes the physical separation, the sample portion only comprises said single type of microorganisms of interest selected or said set of different microorganisms of interest selected.

6. The cultivation method of claim 1, comprising a repeated cycle of the steps (a)-(d).

7. The cultivation method of claim 1, wherein the at least one microorganism of interest is the cyanobacterium *Aphanizomenon flos-aquae* (AFA).

8. A facility for carrying out the method of claim 1 for cultivating said at least one microorganism of interest, by heterotrophy or mixotrophy, comprising:

at least one open or closed culture compartment configured to receive the aqueous culture medium, said at least one microorganism of interest and the contaminating microorganisms;

at least one separating apparatus configured to perform at least one physical separation of said at least one microorganism of interest and the contaminating microorganisms within the portion of the aqueous culture medium;

a lysis device configured to perform a lysis of the contaminating microorganisms separated by said at least one physical separation to produce the lysate; and a transport device configured to at least sample the portion of the aqueous culture medium comprising said at least one microorganism of interest and the contaminating microorganisms, and configured to reintroduce the lysate into said at least one open or closed culture compartment.

9. The cultivation facility of claim 8, wherein the transport device is further configured to:

unify the lysate with said at least one microorganism of interest, separated by said at least one physical separation, to form a mixture and reintroduce the mixture into said at least one open or closed culture compartment; and supply an organic carbon to the aqueous culture medium directly into said at least one open or closed culture compartment, into the lysate, into the mixture or to said at least one microorganism of interest separated by said at least one physical separation.

10. The cultivation facility of claim 8, further comprising at least one concentration system configured to concentrate the contaminating microorganisms separated by said at least one physical separation.

11. The cultivation facility of claim 8, further comprising a first drainer to drain the contaminating microorganisms, a second drainer to drain the aqueous culture medium devoid of the contaminating microorganisms and of said at least one microorganism of interest and a collection device to collect said at least one microorganism of interest.

* * * * *